US009309494B2

(12) United States Patent
Fan et al.

(10) Patent No.: US 9,309,494 B2
(45) Date of Patent: *Apr. 12, 2016

(54) METHOD FOR MAKING NERVE GRAFT (75) Inventors: Li Fan, Beijing (CN); Chen Feng, Beijing (CN); Wen-Mei Zhao, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/981,581

(22) Filed: Dec. 30, 2010

(65) Prior Publication Data

US 2012/0149113 A1    Jun. 14, 2012

(30) Foreign Application Priority Data

Dec. 11, 2010    (CN) .......................... 201010583497.6

(51) Int. Cl.
*C12N 5/079*    (2010.01)
*C12N 5/0793*   (2010.01)
*A61L 27/34*    (2006.01)
*A61L 27/38*    (2006.01)

(52) U.S. Cl.
CPC .............. *C12N 5/0619* (2013.01); *A61L 27/34* (2013.01); *A61L 27/383* (2013.01); *A61L 27/3878* (2013.01); *A61L 2400/12* (2013.01); *A61L 2430/32* (2013.01); *C12N 2533/20* (2013.01); *C12N 2533/32* (2013.01); *C12N 2533/50* (2013.01); *C12N 2535/00* (2013.01)

(58) Field of Classification Search
CPC ... A61L 27/34; A61L 27/383; A61L 27/3878; A61L 2400/12; A61L 2430/32; C12N 5/0619; C12N 2535/00; C12N 2533/20; C12N 2533/32
See application file for complete search history.

(56) References Cited

U.S. PATENT DOCUMENTS

| 6,479,052 | B1* | 11/2002 | Marshall et al. | ............. 424/93.7 |
| 2005/0095695 | A1* | 5/2005 | Shindler et al. | ............. 435/285.1 |
| 2006/0204738 | A1* | 9/2006 | Dubrow et al. | ............. 428/292.1 |
| 2010/0124645 | A1* | 5/2010 | Jiang et al. | ..................... 428/220 |
| 2010/0144004 | A1 | 6/2010 | Zhong et al. | |

FOREIGN PATENT DOCUMENTS

| CN | 101643702 A | 2/2010 |
| CN | 101693125 A | 4/2010 |
| TW | 200639249 | 11/2006 |
| TW | 201006923 A | 2/2010 |

OTHER PUBLICATIONS

Matsumoto K. et al., Neurite Outgrowths of Neurons with Neurotrophin-Coated Carbon Nanotubes, Journal of Bioscience and Bioengineering, 2007, vol. 103, No. 3, pp. 216-220.*
Nguyen-Vu T.D.B. et al., Vertically Aligned Carbon Nanofiber Architecture as a Multifunctional 3-D Neural Electrical Interface, IEEE Transactions on Biomedical Engineering, 2007, vol. 54, No. 6, pp. 1121-1128.*
Sorkin R. et al., Compact self-wiring in cultured neural networks, Journal of Neural Engineering, 2006, vol. 3, pp. 95-101.*
Gabay T. et al., Engineered self-organization of neural networks using carbon nanotube clusters, Physica A, 2005, vol. 350, pp. 611-621.*
Liu K. et al., Controlled Growth of Super-Aligned Carbon Nanotube Arrays for Spinning Continuous Unidirectional Sheets with Tunable Physical Properties, Nano Letters, 2008, vol. 8, No. 2, pp. 700-705.*
Seidlits S.K. et al., Nanostructured scaffolds for neural applications (Review), Nanomedicine, 2008, vol. 3, No. 2, pp. 183-199.*
Wei, B.Q. et al., Assembly of Highly Organized Carbon Nanotube Architectures by Chemical Vapor Deposition, Chem. Mater., 2003, vol. 15, pp. 1598-1606.*
Sucapane A. et al., Interactions Between Cultured Neurons and Carbon Nanotubes: A Nanoneuroscience Vignette, Journal of Neuroscience, Jun. 1, 2009, vol. 1, No. 1, pp. 10-16.*
Galvan-Garcia P. et al., Robust cell migration and neuronal growth on pristine carbon nanotube sheets and yarns, J. Biomater. Sci. Polymer Edn, 2007, vol. 18, No. 10, pp. 1245-1261.*
Wang K. et al., Neural stimulation with a carbon nanotube microelectrode array, Nano Letters, 2006, vol. 6, No. 9, pp. 2043-2048.*
Sunden E.O. "Carbon Nanotube Synthesis for Microsystems Applications", a Master's Thesis for the degree of Master of Science in Mechanical Engineering, presented on Aug. 2006 to Georgia Institute of Technology, pp. i-xvi, and 1-111.*
Murakami Y. et al., Direct Synthesis of Single-Walled Carbon Nanotubes on Silicon and Quartz Based Systems, The international Symposium on Micro-Mechanical Engineering, Dec. 1-3, 2003, pp. 1-8.*
Roberts A.—"Aerosol Delivery of Mammalian Cells for Tissue Engineering", a Thesis for the degree of Masters of Science submitted to Worcester Polytechnic Institute, Apr. 2003, pp. 1-65.*
F,Yang.et al."Electrospinning of nano/micro scale poly(L-lactic acid) aligned fibers and their potential in neural tissue engineering"; Biomaterials; vol. 26, 2005, pp. 2603-2610.
Sensenbrenner M, et al.;"Neuronal cells from chick embryo cerebral hemisp heres cultivated on polylysine-coated surfaces"; Developmental Neuroscience, vol. 1, No. 2, p. 90-101, 1978, Abst only.
Zhang Jinchao et al. "Application of Nanomaterials in Tissue Engineering" Progress in Chemistry, vol. 22 No. 11, Nov. 2010, pp. 2232-2237.
Weijie Huang et al. "Attaching Proteins to Carbon Nanotubes via Diimide-Activated Amidation" Nano Letters, 2002, vol. 2, No. 4 pp. 311-314.
Xuan Zhang et al. "Guided neurite growth on patterned carbon nanotubes" Sensors and Actuators B, vol. 106, 2005 pp. 843-850.

(Continued)

Primary Examiner — Satyendra K Singh
(74) Attorney, Agent, or Firm — Novak Druce Connolly Bove + Qugg LLP (57) ABSTRACT

A method for making a nerve graft includes the following steps. A culture layer including a carbon nanotube film structure and a protein layer is provided. The protein layer is located on a surface of the carbon nanotube film structure. A number of nerve cells are seeded on a surface of the protein layer away from the carbon nanotube film structure. The nerve cells are cultured until a number of neurites branch from the nerve cells and are connected between the nerve cells.

16 Claims, 12 Drawing Sheets

(56) References Cited

OTHER PUBLICATIONS

Kotaro Matsumoto et al. "Neurite outgrowths of neurons with neurotrophin-caoted carbon nanotubes" J. Biosci. Bioeng., 103, 2007, pp. 216-220.

Nguyen-Vu et al. "Vertically Aligned Carbon Nanofiber Architecture as a Multifunctional 3-D Neural Electrical Interface" IEEE Transactions on Biomedical Engineering, Vol. 54, No. 6, Jun. 2007. pp. 1121-1128.

Tamir Gabay et al. "Engineered selforganization of neural networks using carbon nanotube clusters" Physica A 350; 2005; pp. 611-621.

Stephanie K Seidlits et al. "Nanostructured scaffolds for neural applications"; Nanomedicine; 2008; vol. 3 Tssue:2; pp. 183-199.

R Sorkin, et al. "Compact self-wiring in cultured neural networks"; Journal of Neural Engineering; Apr. 11, 2006; vol. 3 Issue:2 pp. 95-101.

\* cited by examiner

METHOD FOR MAKING NERVE GRAFT

CROSS-REFERENCES TO RELATED APPLICATIONS

This application claims all benefits accruing under 35 U.S.C. §119 from China Patent Application No. 201010583497.6, filed on Dec. 11, 2010, in the China Intellectual Property Office, the disclosure of which is incorporated herein by reference. This application is related to commonly-assigned application Ser. No. 12/981,572, entitled, "METHOD FOR MAKING NERVE GRAFT," filed on Dec. 30, 2010; Ser. No. 12/981,573, entitled, "NERVE GRAFT," filed on Dec. 30, 2010, and Ser. No. 12/981,584, entitled, "NERVE GRAFT," filed on Dec. 30, 2010.

BACKGROUND

1. Technical Field

The present disclosure relates to a method for making a biological graft, especially to a method for making a nerve graft.

2. Description of Related Art

A nervous system is a complex cellular communication network that is mainly composed of neurons and glial cells (neuroglial cells). Glial cells occupy spaces between neurons and modulate neurons' functions. The neuron sense features of both external and internal environments and transmit this information to the brain for processing and storage. For example, the neurons receive the diverse types of stimuli from the environment (e.g. light, touch, sound) and convert into electric signals, which are then converted into chemical signals to be passed on to other cells.

Neurons exist in a number of different shapes and sizes, and can be classified by their morphology and function. The basic morphology of a neuron includes a cell body and neurites projecting/branching from the cell body towards other neurons. The neurites also can be defined into two types by their functions. One is a dendrite, which branches around the cell body and receive signals from other neurons to cell body. The other is an axon, which branches from the cell body and grows continually without tapering. The axon conducts the signals away from the neuron's cell body. The end of the axon has branching terminals that release neurotransmitter substances acting as chemical signals into a gap between the branching terminals and the dendrites of other neurons. Thus, the information or signal is propagated.

Once injury to the nervous system occurs, neuron damage will lead to neurite degeneration and retraction. If the damage is severe, breaks in neurites of the neuron are presented. Consequentially, the signal transmission will be affected and the cellular communication with specific neurons will cease. Generally, damage on the neurites will reverse by introducing nerve pipes including degradable biological material to the nervous system to reconnect with the opposite terminals in broken neurites. The neurites grow along the nerve pipes until the neurites are combined together. Thus, the neuron damage is reversed.

However, if a distance between the broken neurites is long, a growing time of the neurites can be long, thus a long recovery time for reversing the neuron damage is required What is needed, therefore, is to provide a method for making a nerve graft, to overcome the above-described shortcomings.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings. It should be noted that references to "an" or "one" embodiment in this disclosure are not necessarily to the same embodiment, and such references mean at least one.

Figure 1:
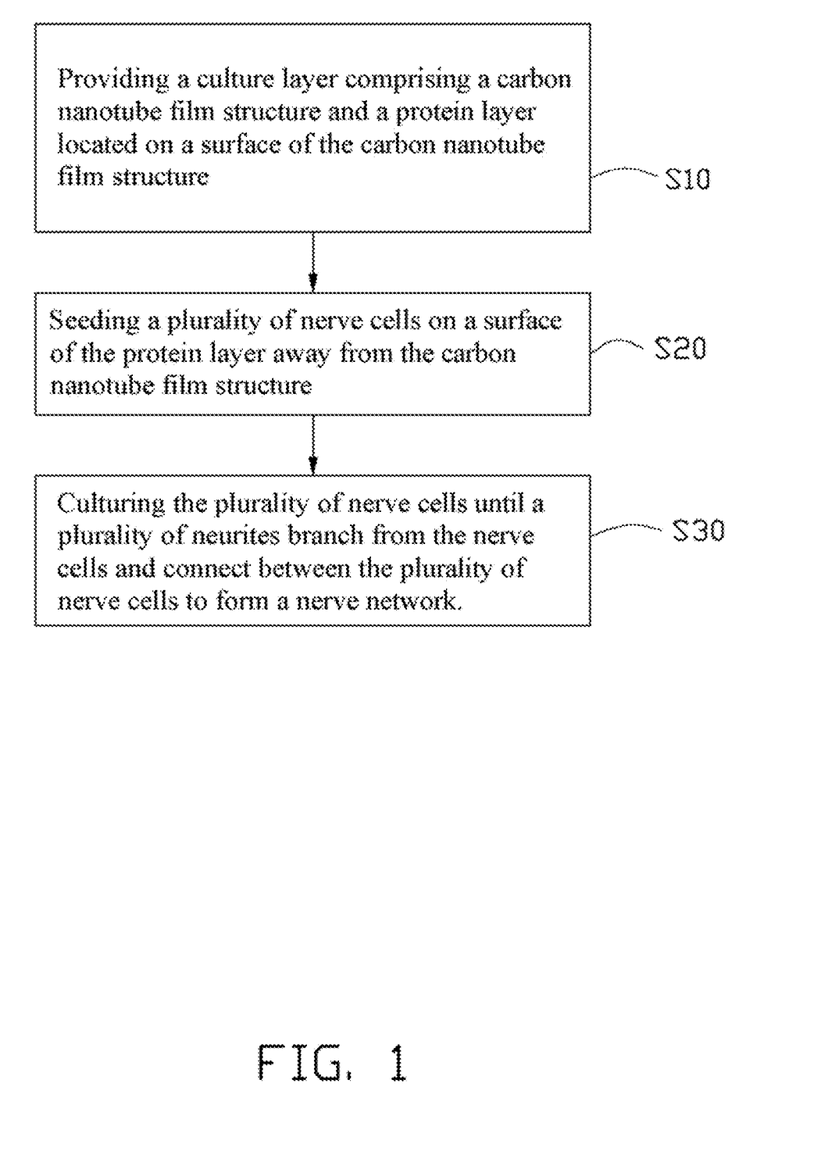
FIG. 1 shows a schematic structural view of a flow chart of one embodiment of a method for making a nerve graft.

A method for making a nerve graft of one embodiment can include the following steps:

S10, providing a culture layer comprising a carbon nanotube film structure and a protein layer located on a surface of the carbon nanotube film structure;

S20, seeding a plurality of nerve cells on a surface of the protein layer away from the carbon nanotube film structure; and S30, culturing the plurality of nerve cells until a plurality of neurites branch from the nerve cells and connect between the plurality of nerve cells to form a nerve network.

In step S10, the carbon nanotube film structure can be capable of forming a free-standing structure. The term "free-standing structure" can be defined as a structure that does not have to be supported by a substrate. For example, a free-standing structure can sustain the weight of itself if the free-standing structure is hoisted by a portion thereof without any significant damage to its structural integrity. The carbon nanotubes distributed in the carbon nanotube film structure defines a plurality of gaps therebetween. An average gap can be in a range from about 0.2 nanometers to about 9 nanometers. The carbon nanotubes can have a significant van der Waals attractive force therebetween. The free-standing structure of the carbon nanotube film structure is realized by the carbon nanotubes joined by van der Waals attractive force. As such, if the carbon nanotube film structure is placed between two separate supporters, a portion of the carbon nanotube film structure not in contact with the two supporters, would be suspended between the two supporters and yet maintain film structural integrity.

The carbon nanotubes in the carbon nanotube film structure can be orderly or disorderly arranged. The term 'disordered carbon nanotube film structure' includes, but is not limited to, a structure where the carbon nanotubes are arranged along many different directions such that the number of carbon nanotubes arranged along each different direction can be almost the same (e.g. uniformly disordered), and/or entangled with each other. 'Ordered carbon nanotube film structure' includes, but is not limited to, a structure where the carbon nanotubes are arranged in a consistently systematic manner, e.g., the carbon nanotubes are arranged approximately along a same direction and or have two or more sections within each of which the carbon nanotubes are arranged approximately along a same direction (different sections can have different directions). The carbon nanotubes in the carbon nanotube film structure can be single-walled, double-walled, and/or multi-walled carbon nanotubes.

Macroscopically, the carbon nanotube film structure may have a substantially planar structure. The planar carbon nanotube film structure can have a thickness of about 0.5 nanometers to about 100 microns. The carbon nanotube film structure includes a plurality of carbon nanotubes and defines a plurality of micropores having a size of about 1 nanometer to about 500 nanometers. The carbon nanotube film structure includes at least one carbon nanotube film, the at least one carbon nanotube film includes a plurality of carbon nanotubes substantially parallel to a surface of the corresponding carbon nanotube film. The carbon nanotube film structure can include at least one carbon nanotube film. If the carbon nanotube film structure includes a plurality of carbon nanotube films stacked together, adjacent carbon nanotube films can only be adhered by van der Waals attractive force therebetween.

Figure 2:
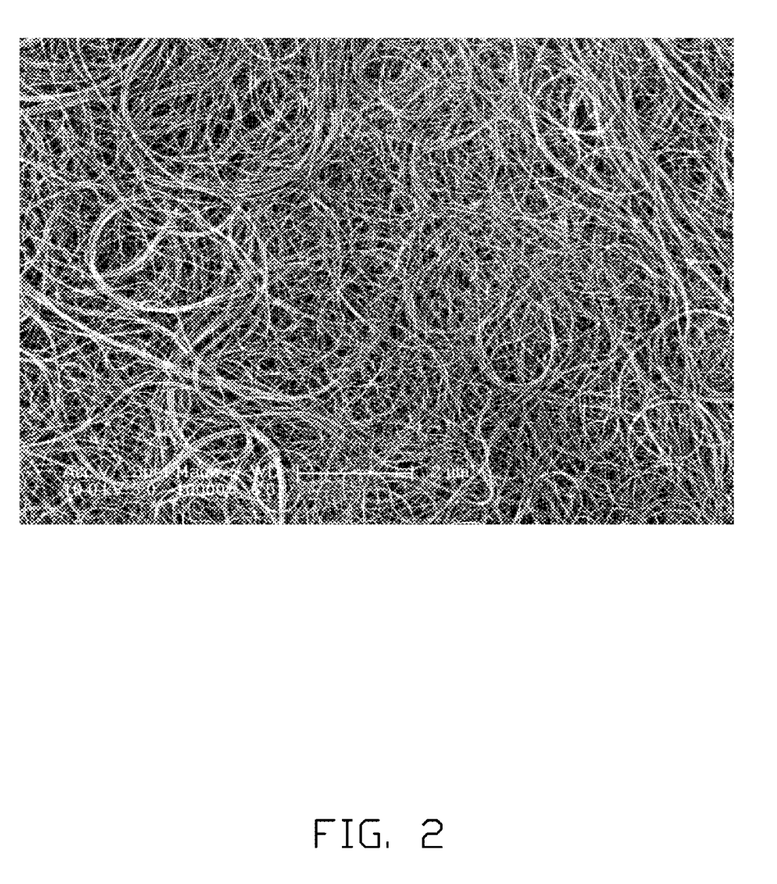
FIG. 2 shows a Scanning Electron Microscope (SEM) image of a flocculated carbon nanotube film.

The carbon nanotube film structure can include a flocculated carbon nanotube film as shown in FIG. 2. The flocculated carbon nanotube film can include a plurality of long, curved, disordered carbon nanotubes entangled with each other and can form a free-standing structure. Further, the flocculated carbon nanotube film can be isotropic. The carbon nanotubes can be substantially uniformly dispersed in the flocculated carbon nanotube film. The adjacent carbon nanotubes are acted upon by the van der Waals attractive force therebetween, thereby forming an entangled structure with micropores defined therein. Alternatively, the flocculated carbon nanotube film is porous. Sizes of the micropores can be about 1 nanometer to about 500 nanometers. Further, due to the carbon nanotubes in the carbon nanotube film structure being entangled with each other, the carbon nanotube film structure employing the flocculated carbon nanotube film has excellent durability and can be fashioned into desired shapes with a low risk to the integrity of the carbon nanotube film structure. The flocculated carbon nanotube film, in some embodiments, will not require the use of a structural support due to the carbon nanotubes being entangled and adhered together by van der Waals attractive force therebetween. The flocculated carbon nanotube film can define a plurality of micropores having a diameter of about 1 nanometer to about 500 nanometers.

Figure 3:
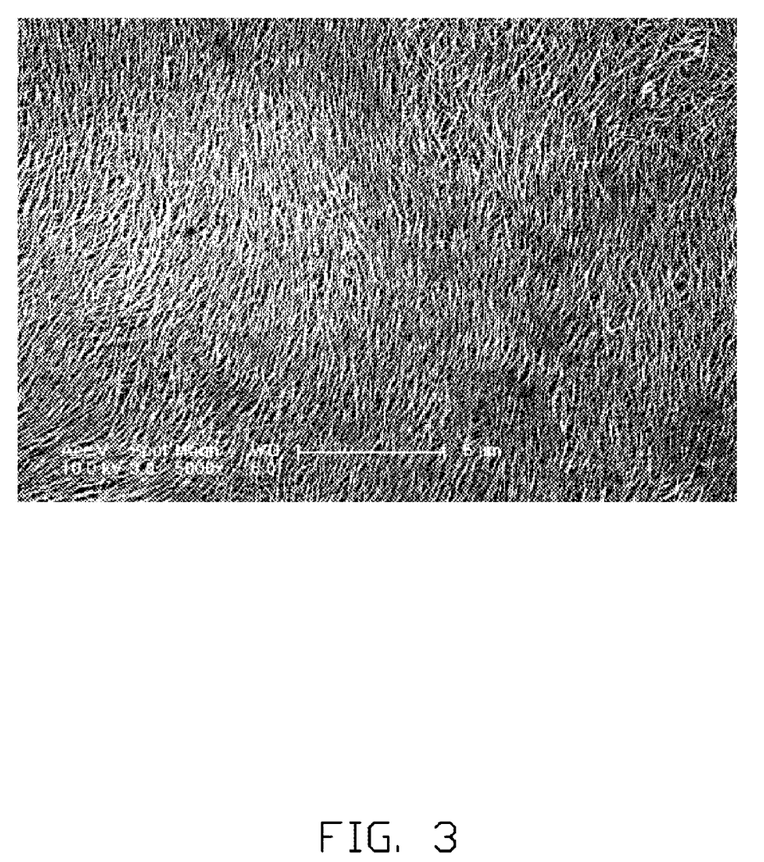
FIG. 3 shows an SEM image of a pressed carbon nanotube film.

The carbon nanotube film structure can include a pressed carbon nanotube film. The carbon nanotubes in the pressed carbon nanotube film can be arranged along a same direction or arranged along different directions. The carbon nanotubes in the pressed carbon nanotube film can rest upon each other. The adjacent carbon nanotubes are combined and attracted to each other by van der Waals attractive force, and can form a free-standing structure. An angle between a primary alignment direction of the carbon nanotubes and a surface of the pressed carbon nanotube film can be in a range from approximately 0 degrees to approximately 15 degrees. The pressed carbon nanotube film can be formed by pressing a carbon nanotube array. The angle is closely related to pressure applied to the carbon nanotube array. The greater the pressure, the smaller the angle. The carbon nanotubes in the carbon nanotube film are substantially parallel to the surface of the carbon nanotube film if the angle is about 0 degrees. A length and a width of the carbon nanotube film can be set as desired. The pressed carbon nanotube film can include a plurality of carbon nanotubes substantially aligned along one or more directions. The pressed carbon nanotube film can be obtained by pressing the carbon nanotube array with a pressure head. Alternatively, the shape of the pressure head and the pressing direction can determine the direction of the carbon nanotubes arranged therein. Specifically, in one embodiment, a planar pressure head is used to press the carbon nanotube array along the direction substantially perpendicular to a substrate. A plurality of carbon nanotubes pressed by the planar pressure head may be sloped in many directions. In another embodiment, as shown in FIG. 3, if a roller-shaped pressure head is used to press the carbon nanotube array along a certain direction, the pressed carbon nanotube film having a plurality of carbon nanotubes substantially aligned along the certain direction can be obtained. In another embodiment, if the roller-shaped pressure head is used to press the carbon nanotube array along different directions, the pressed carbon nanotube film having a plurality of carbon nanotubes substantially aligned along different directions can be obtained. The pressed carbon nanotube film can define a plurality of micropores having a diameter of about 1 nanometer to about 500 nanometers.

Figure 4:
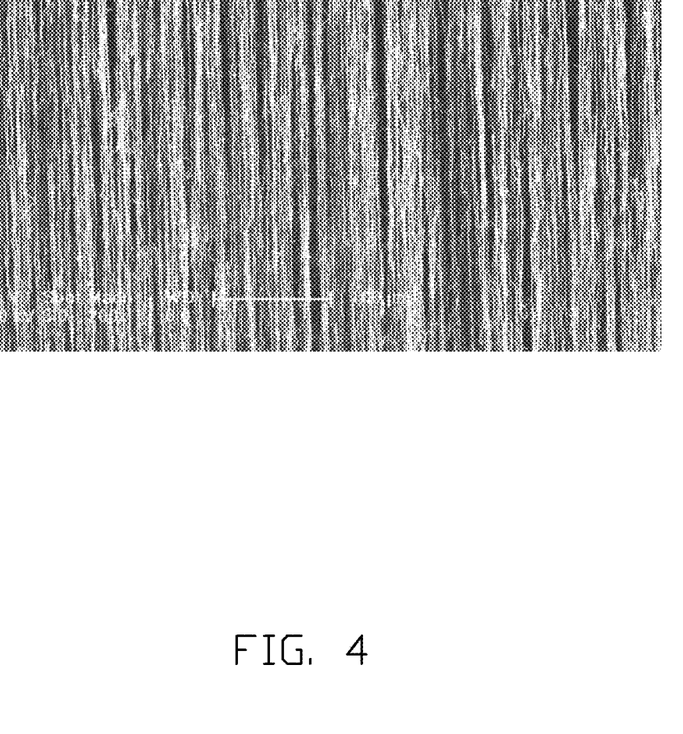
FIG. 4 shows an SEM image of a drawn carbon nanotube film.

In some embodiments, the carbon nanotube film structure includes at least one drawn carbon nanotube film as shown in FIG. 4. The drawn carbon nanotube film can have a thickness of about 0.5 nanometers to about 100 microns. The drawn carbon nanotube film includes a plurality of carbon nanotubes that can be arranged substantially parallel to a surface of the drawn carbon nanotube film. A plurality of micropores having a size of about 1 nanometer to about 500 nanometers can be defined by the carbon nanotubes. A large number of the carbon nanotubes in the drawn carbon nanotube film can be oriented along a preferred orientation, meaning that a large number of the carbon nanotubes in the drawn carbon nanotube film are arranged substantially along the same direction. An end of one carbon nanotube is joined to another end of an adjacent carbon nanotube arranged substantially along the same direction, by van der Waals attractive force. More specifically, the drawn carbon nanotube film includes a plurality of successively oriented carbon nanotube segments joined end-to-end by van der Waals attractive force therebetween. Each carbon nanotube segment includes a plurality of carbon nanotubes substantially parallel to each other and joined by van der Waals attractive force therebetween. The carbon nanotube segments can vary in width, thickness, uniformity, and shape. A small number of the carbon nanotubes are randomly arranged in the drawn carbon nanotube film and has a small if not negligible effect on the larger number of the carbon nanotubes in the drawn carbon nanotube film arranged substantially along the same direction.

Understandably, some variation can occur in the orientation of the carbon nanotubes in the drawn carbon nanotube film as can be seen in FIG. 3. Microscopically, the carbon nanotubes oriented substantially along the same direction may not be perfectly aligned in a straight line, and some curve portions may exist. Furthermore, it can be understood that some carbon nanotubes are located substantially side by side and oriented along the same direction and in contact with each other.

The carbon nanotube film structure can include a plurality of stacked drawn carbon nanotube films. Adjacent drawn carbon nanotube films can be adhered by only the van der Waals attractive force therebetween. An angle can exist between the carbon nanotubes in adjacent drawn carbon nanotube films. The angle between the aligned directions of the adjacent drawn carbon nanotube films can range from 0 degrees to about 90 degrees. In one embodiment, the angle between the aligned directions of the adjacent drawn carbon nanotube films is substantially 90 degrees. Simultaneously, aligned directions of adjacent drawn carbon nanotube films can be substantially perpendicular to each other, thus a plurality of micropores and nodes can be defined by the carbon nanotube film structure.

The protein layer is positioned on the carbon nanotube film structure, to form a hydrophilic and bio-compatible surrounding on the carbon nanotube film structure. The protein layer can include fibrous protein, enzyme protein, or blood serum. The protein layer can include soluble protein and insoluble protein. The term "soluble protein" can be defined as protein that is capable of interacting with water. In one embodiment, there can be a plurality of hydrophilic amino acids disposed on the outer surface of the soluble protein to interact with water. In one embodiment, the protein layer includes blood serum of a mammal, such as a cow, a pig, or human. The blood serum cannot only define a hydrophilic and bio-compatible surrounding on the carbon nanotube film structure, but can also supply a cell growth factor for the nerve cells or the nerve network.

Means for fabricating the culture layer is not limited, provided the protein layer and the carbon nanotube film structure are mixed together. For example, the culture layer can be fabricated by soaking the carbon nanotube film structure with a protein solution. Thus, the protein solution can be a pure protein, or a solution including the protein and a biological media dissolving the protein.

If the carbon nanotube film structure is soaked by the protein solution, the protein solution can infiltrate into the micropores defined in the carbon nanotube film structure. Thus, the carbon nanotubes of the carbon nanotube film structure can be soaked by the protein solution. Therefore, the carbon nanotubes can be wrapped by the protein layer. Alternatively, the protein layer can wrap all of the carbon nanotubes or part of the carbon nanotubes, provided the protein layer can cover at least part of the surface of the carbon nanotube film structure. Thus, the carbon nanotube film structure needs not be in contact with the nerve network directly. The carbon nanotube film structure is a lyophobic article and is not capable of defining a hydrophilic and bio-compatible surrounding to form the nerve network thereon or acting as a biological substrate. Thus, as long as the protein layer is located on the carbon nanotube film structure to form the culture layer, the nerve network can be located on the carbon nanotube film structure.

In one embodiment, the culture layer is fabricated by the following steps:

S11, providing the carbon nanotube film structure; and

S12, soaking the carbon nanotube film structure with a protein solution to form the protein layer.

In step S12, means for soaking the carbon nanotube film structure with the protein solution is not limited, provided the protein of the protein solution can be adhered to the surface of the carbon nanotube structure to form the protein layer. For example, the protein solution can be sprayed on the surface of the carbon nanotube film structure, to soak the carbon nanotube film structure with the protein solution. In one embodiment, to soak the carbon nanotube film structure with the protein solution, the step S12 includes a step of dipping the carbon nanotube film structure into the protein solution. A dipping time is not limited, provided most of the carbon nanotubes of the carbon nanotube film structure are soaked with the protein solution and the protein does not deteriorate. In one embodiment, the carbon nanotube film structure is dipped in a cow's blood serum for about 1.5 hours.

When the carbon nanotube film structure is dipped in the protein solution, part of the carbon nanotubes or all of the carbon nanotubes can be soaked by the protein solution. The longer the dipping time, the more the carbon nanotubes of the carbon nanotube film structure can be soaked by the protein solution. The smaller a thickness of the carbon nanotube film structure, the more the carbon nanotubes of the carbon nanotube film structure can be soaked by the protein solution.

The step S10 can further include a step of S13, sterilizing the protein layer. Means for sterilizing the protein layer is not limited, provided nearly all of the bacteria distributed in the protein layer can be killed. The protein layer can be sterilized by means of an ultraviolet sterilization technology or a high temperature sterilization technology. If the protein layer is sterilized by means of high temperature sterilization technology, a temperature of the protein layer should be less than about 220 degrees, thus the protein layer cannot be damaged. In one embodiment, the temperature of the protein layer is about 120 degrees. A rigidity of the protein layer can be increased if the protein layer is sterilized because part of the water in the protein layer can be evaporated.

The step S10 can further include a step of S14: introducing a poly-D-lysine (PDL) layer on a surface of the protein layer away from the carbon nanotube film structure. In the step S14, the poly-D-lysine layer can increase an adhesive attraction force between the culture layer and the nerve cells by forming a plurality of changes on the surface of the culture layer. The poly-D-lysine layer can be formed by dipping the protein layer located on the carbon nanotube film structure into a poly-D-lysine solution. A concentration of the poly-D-lysine in the poly-D-lysine solution can be about 20 milligrams per milliliter.

In the step S20, the nerve cells can be from a mammal, such as a human, a mouse, or a cow. The nerve cells are neurons. In one embodiment, the nerve cells are hippocampal neurons from a mouse. The nerve cells can be seeded on the protein layer by spraying a nerve cells solution to the surface of the protein layer, or by dipping the culture layer into the nerve cells solution. If the culture layer is dipped into the nerve cells solution, the nerve cells solution can be received in a culture dish and the protein layer is not in contact with the culture dish. In one embodiment, a surface of the carbon nanotube film structure away from the protein layer is in contact with a lyophobic substrate positioned on the culture dish. The lyophobic substrate can separate the protein layer and the culture dish. The lyophobic substrate can be a silica gel substrate or a substrate coated with silica gel. When the protein layer is covered by the cells solution, the nerve cells in the nerve cells solution can be deposited or seeded on the surface of the protein layer.

In step S30, surrounding conditions for culturing the nerve cells are not limited, provided the neurites can branch from the nerve cells and be connected between the nerve cells. The nerve cells can be cultured under room temperature and an atmospheric pressure. The nerve cells can also be cultured under a condition similar to a condition in a mammal Cell growth factors can be provided by the protein layer to culture the nerve cells. Alternatively, the carbon nanotube film structure cannot define the growth surrounding for the nerve cells, thus, the nerve cells can only be cultured on the surface of the carbon nanotube film structure with the protein layer thereon. The nerve network can only be located on the carbon nanotube film structure with the protein layer thereon and combined with the carbon nanotube film structure.

The neurites can include dendrites or axons. Generally, the neurites can grow in all directions from one nerve cell. But if there is a plurality of nerve cells located on the surface of the protein layer, the neurites from one nerve cell would preferentially extend to adjacent nerve cells. Thus, growth directions of the neurites can be guided by positions of the nerve cells.

In the method for making the nerve graft, the culture layer can define a growth surrounding of the nerve cells, thus the nerve network can be formed on the culture layer. Both of the protein layer and the carbon nanotube film can have good tactility, and nonmetal and bio-compatible properties. Thus, the culture layer including the protein layer and the carbon nanotube film structure can be transplanted into a biological body and form a shape as desired. Therefore, the shape and a thickness of the culture layer can be designed as a shape and a thickness of a wound of the biological body, such as a human wound. The nerve cells of the nerve network can communicate with each other, thus, if the nerve graft is transplanted into the wound, nerve cells of the biological body close to the wound and the nerve network can be connected together. An area of the wound can be substantially equal to an area of the nerve graft, and a distance between an edge of the nerve graft and an edge of the wound can be less than a length of the wound. Therefore, a distance between the nerve cells of the biological body close to the wound and the nerve network can be less than the length of the wound. The less the distance between the nerve cells of the biological body close to the wound and the nerve network, the less the time of connecting the nerve network and the nerve cells of the biological body, the less the time recovering the wound.

In addition, generally, the carbon nanotubes are pure carbon nanotubes consisting primarily of carbon atoms. The carbon nanotubes can also include carbon nanotubes that are modified, to form a plurality of functional groups, such as hydrophilic functional groups. But the functional groups do not contribute to the method for making the nerve graft, because the functional groups are substantially covered or wrapped by the protein layer.

Figure 5:
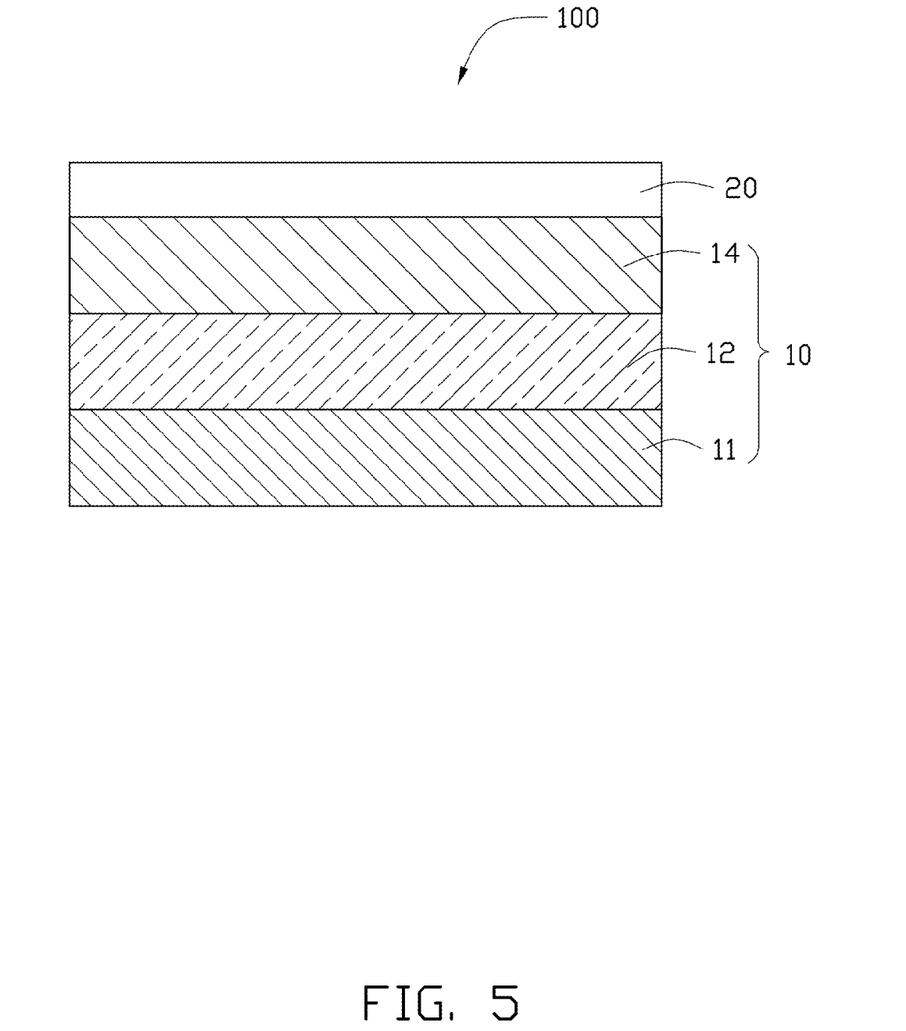
FIG. 5 shows a side view of the nerve graft.

The nerve graft of one embodiment can be fabricated by the method mentioned above. Referring to FIG. 5, the nerve graft 100 can include a culture layer 10 and a nerve network 20 located on a surface of the culture layer 10.

The culture layer 10 includes a carbon nanotube film structure 12, and a protein layer 14. The protein layer 14 is located on a surface of the carbon nanotube film structure 12.

Macroscopically, the carbon nanotube film structure 12 is a planar structure and capable of forming a free-standing structure. The carbon nanotube film structure 12 includes a plurality of carbon nanotubes substantially parallel to a surface of the corresponding carbon nanotube film structure 12. The carbon nanotube film structure 12 can include at least one carbon nanotube film. If the carbon nanotube film structure 12 includes a plurality of carbon nanotube films, the carbon nanotube films can be stacked together, and adjacent carbon nanotube films can be adhered by only van der Waals attractive force therebetween. The carbon nanotube film can be a flocculated carbon nanotube film as shown in FIG. 2, a pressed carbon nanotube film as shown in FIG. 3, and a drawn carbon nanotube film as shown in FIG. 4. In one embodiment, the carbon nanotube film structure 12 includes a plurality of drawn carbon nanotube films stacked together. Aligned directions of adjacent drawn carbon nanotube films are substantially perpendicular to each other. A thickness of the carbon nanotube film structure 12 is not limited. Generally, the thickness of the carbon nanotube film structure 12 can be from about 0.3 micrometers to about 60 micrometers. In one embodiment, the thickness of the carbon nanotube film structure 12 is about 0.6 micrometers.

The protein layer 14 can include fibrous protein, enzyme protein, or blood serum. The protein layer 14 can include soluble protein and insoluble protein. The term "soluble protein" can be defined as a protein capable of interacting with water. There can be a plurality of hydrophilic amino acids disposed on the outer surface of the soluble protein. In one embodiment, the protein layer 14 includes blood serum of a mammal, such as a cow, a pig, or human. The blood serum cannot only be capable of defining a hydrophilic and biocompatible surrounding on the carbon nanotube film structure 12, but also capable of supplying a cell growth factor for the nerve cells or the nerve network 20.

A thickness of the protein layer 14 is not limited, provided the hydrophilic and biocompatible surrounding can be defined on the carbon nanotube film structure 12. The thickness of the protein layer 14 can be from about 0.3 micrometers to about 2 micrometers. In one embodiment, the thickness of the protein layer 14 is about 0.6 micrometers. Macroscopically, the protein layer 14 is located on a surface of the carbon nanotube film structure 12 away from the lyophobic substrate 11. Microscopically, the protein layer 14 can penetrate into the carbon nanotube film structure 12 and wrap part of or all of the carbon nanotubes of the carbon nanotube film structure 12. Therefore, an obvious interface cannot be defined between the carbon nanotube film structure 12 and the protein layer 14. The less the thickness of the carbon nanotube film structure 12, the more the carbon nanotube film structure 12 can be wrapped by the protein layer 14.

Figure 6:
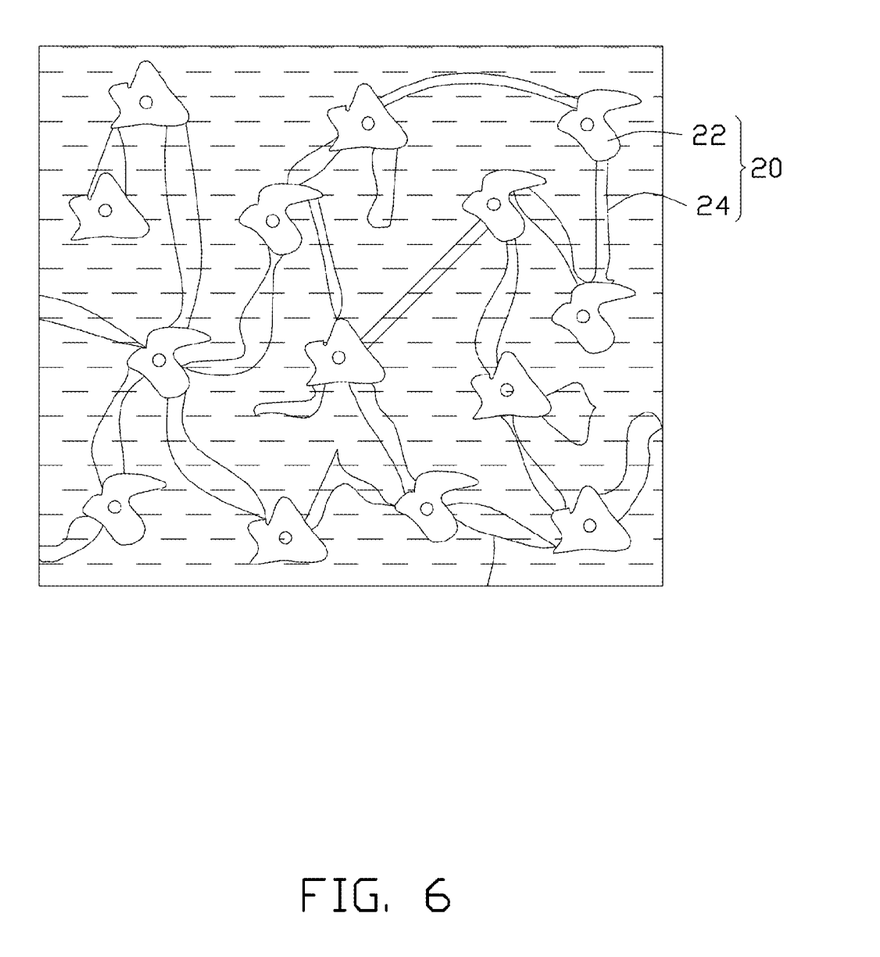
FIG. 6 shows a top view of the nerve graft.

The nerve network 20 is disposed on a surface of the protein layer 14 away from the lyophobic substrate 11. The neurites 24 can be dendrites or axons. The nerve network 20 includes a plurality of nerve cells 22 and a plurality of neurites 24 branching from the nerve cells 22 and connected among the nerve cells 22. The number of the neurites 24 branching from each of the nerve cells 22 is not limited, provided at least two nerve cells 22 are connected by at least one neurite 24. Each of the neurites 22 can be connected between two neurites 24, or be connected to only one neurite 24, provided at least two nerve cells 22 are connected by at least one neurite 24.

The culture layer 10 combining with the nerve network 20 can have good tactility, nonmetal and biocompatible properties, thus the culture layer 10 can be transplanted into a biological body, such as human. Thus, a shape and a thickness of the nerve graft 100 can be designed as a shape and a thickness of a wound of the biological body. The nerve cells 22 of the nerve network 20 can communicate with each other by the neurites 24, thus if the nerve graft 100 is transplanted into the wound, nerve cells 22 of the biological body close to the wound and the nerve network 20 can be connected together. An area of the wound can be substantially equal to an area of the nerve graft 100, and a distance between an edge of the nerve graft 100 and an edge of the wound can be less than the length of the wound. Therefore, a distance between the nerve cells 22 of the biological body close to the wound and the nerve network 20 can be less than the length of the wound. The less the distance between the nerve cells 22 of the biological body close to the wound and the nerve network 20, the less time it takes to connect the nerve network 20 and the nerve cells 22 of the biological body with the neurites 24, and the less the time it takes for the wound to heal.

A method for making a nerve graft of one detailed embodiment can include the following steps:

S210, providing a carbon nanotube film structure;

S220, dipping the carbon nanotube film structure into cow blood serum to soak the carbon nanotube film structure with the cow blood serum, thus allowing a cow blood serum layer to form the carbon nanotube film structure;

S230, taking the carbon nanotube film structure coated with the cow blood serum layer out of the cow blood serum solution, and sterilizing the cow blood serum layer at a temperature of about 120 degrees;

S240, dipping the sterilized cow blood serum layer into a poly-D-lysine solution to form a poly-D-lysine layer on the cow blood serum layer, and thus a culture layer including the carbon nanotube film structure, the protein layer, and the poly-D-lysine layer is formed;

S250, covering the culture layer with a nerve cell solution until a plurality of nerve cells 22 dissolved in the nerve cell solution are deposited or seeded on a surface of the poly-D-lysine layer away from the carbon nanotube film structure; and S260, culturing the plurality of nerve cells 22 until a plurality of neurites 24 branch from the nerve cells 22 and connect among the plurality of nerve cells 22.

Figure 7:
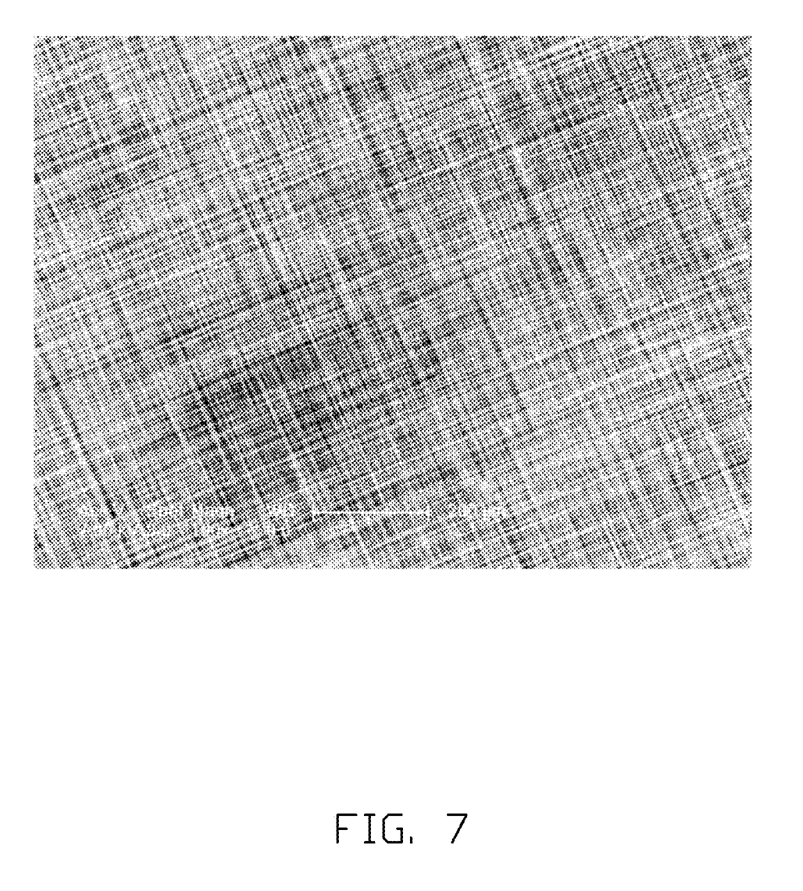
FIG. 7 shows an SEM image of a carbon nanotube film structure including a plurality of stacked drawn carbon nanotube films.
Figure 8:
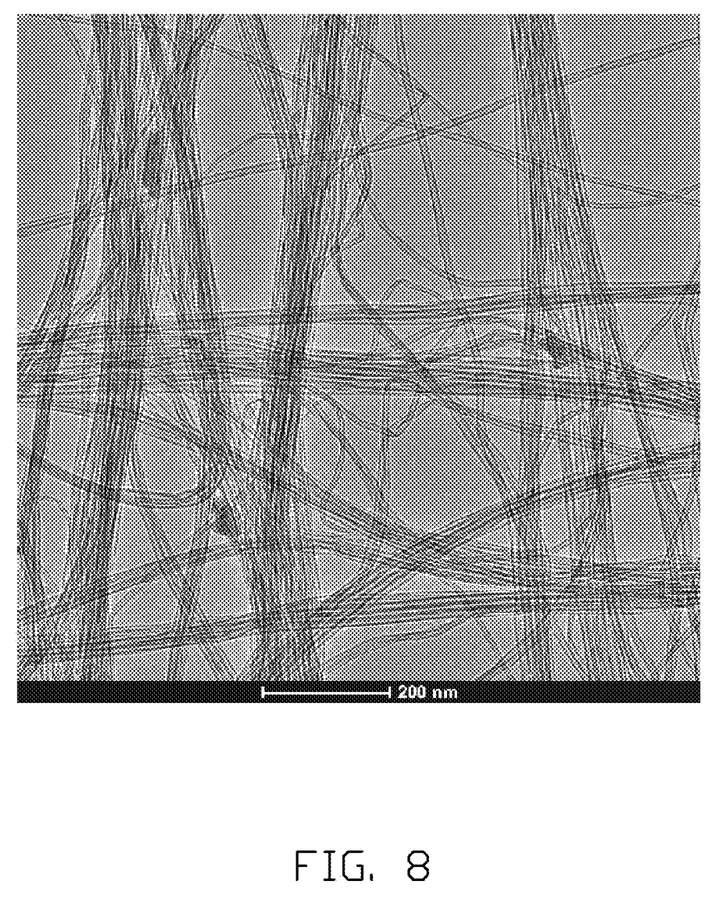
FIG. 8 shows a Transmission Electron Microscope (TEM) image of the carbon nanotube film structure.

Referring to FIG. 7 and FIG. 8, the carbon nanotube film structure includes a plurality of drawn carbon nanotube films stacked together, and aligned directions of adjacent drawn carbon nanotube films are substantially perpendicular to each other.

Figure 9:
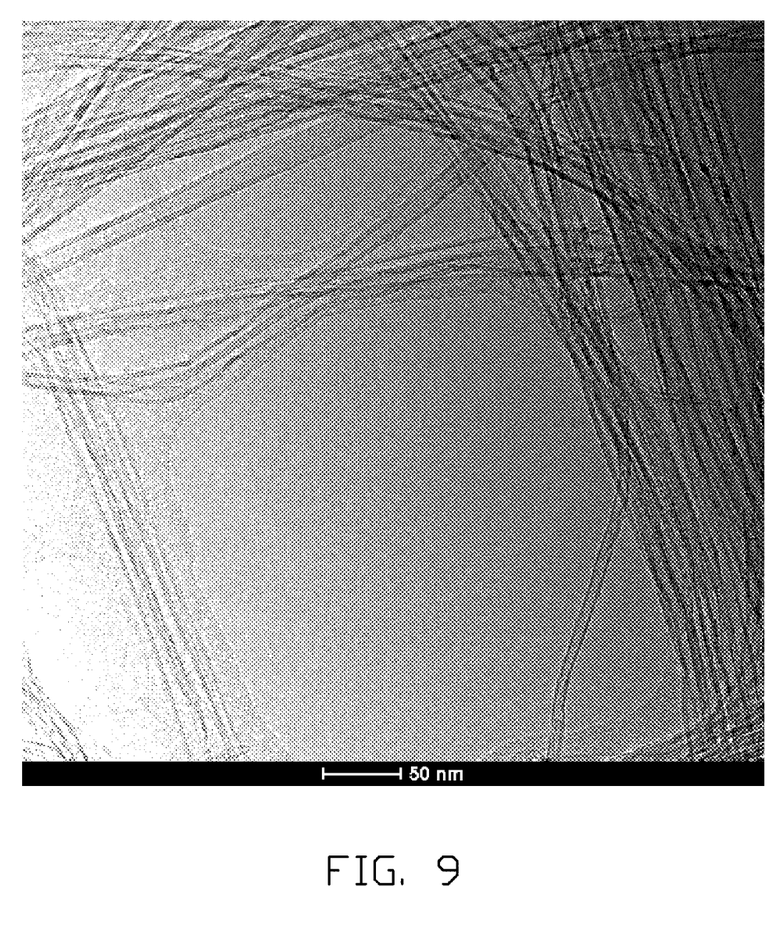
FIG. 9 shows a TEM image of a culture layer.

In step S220, the cow blood serum is pure liquid cow blood serum. A dipping time for dipping the carbon nanotube film structure can be determined by a thickness of the carbon nanotube film structure. The thinner the carbon nanotube film structure, the shorter the dipping time. In one embodiment, the thickness of the carbon nanotube film structure is about 0.6 micrometers, and the dipping time is about 1.5 hours. If the carbon nanotube film structure has a thickness of about 0.6 micrometers dipped in the cow blood serum for about 1.5 hours, the cow blood serum layer can be formed on the carbon nanotube film structure as shown in FIG. 9.

A rigidity of the protein layer can be increased if the protein layer is sterilized under temperature, because part of the water in the protein layer can be evaporated.

In the step S240, the poly-D-lysine layer is disposed on a surface of the cow blood serum layer away from the carbon nanotube film structure. The poly-D-lysine layer can increase an adhesive attraction force between the culture layer and the nerve cells. A concentration of the poly-D-lysine in the poly-D-lysine solution can be about 20 milligrams per milliliter.

In the step S250, the nerve cells 22 can be from a mammal, such as a human, a mouse, or a cow. The nerve cells 22 are neurons. In one embodiment, the nerve cells 22 are hippocampal neurons from a mouse. If the culture layer is dipped into the nerve cells solution, the nerve cells solution can be received in a culture dish and the cow blood serum layer is not in contact with the culture dish. When the cow blood serum layer is covered by the cells solution, the nerve cells 22 in the nerve cells solution can be deposited or seeded on the surface of the cow blood serum layer.

Figure 10:
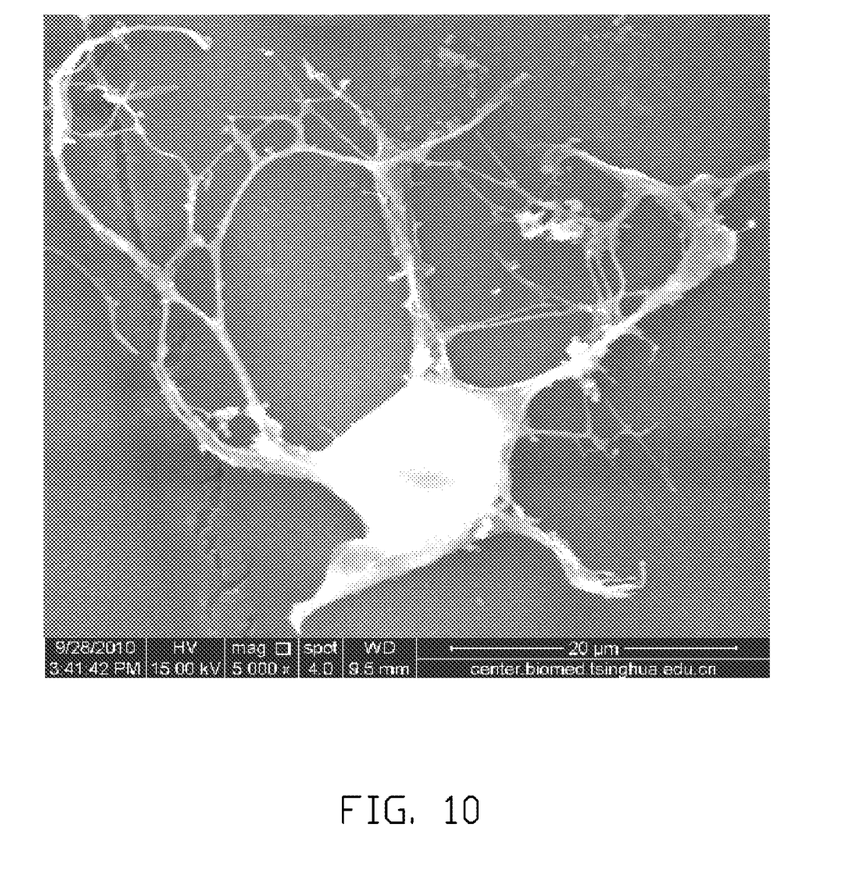
FIG. 10 shows an SEM image of one nerve cell cultured on the culture layer.

In step S260, surrounding conditions for culturing the nerve cells 22 are not limited, provided the neurites 24 can branch from the nerve cells 22 and be connected between the nerve cells 22. The nerve cells 22 can also be cultured under room temperature and an atmospheric pressure. The nerve cells 22 can be cultured under a condition similar to a condition in a mammal Referring to FIG. 10, when one of the nerve cells 22 seeded on the culture layer are cultured in a typical room condition for about 15 days, a plurality of neurites 24 branch from the one of the nerve cells 22.

Figure 11:
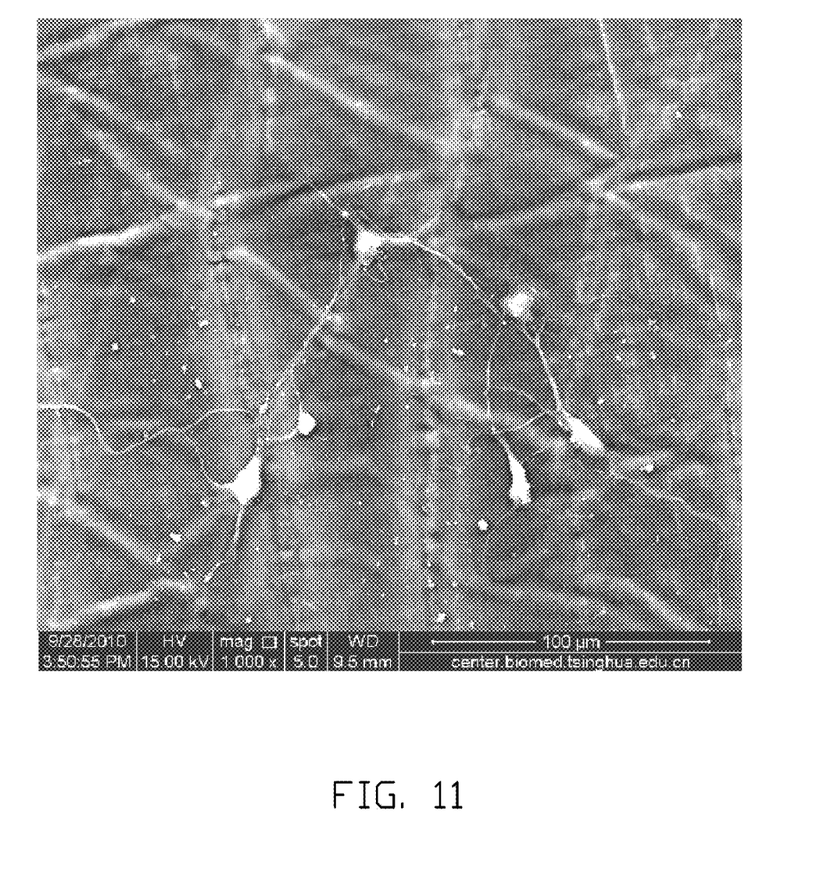
FIG. 11 shows an SEM image of a nerve graft, wherein a nerve network of the nerve graft are dyed.
Figure 12:
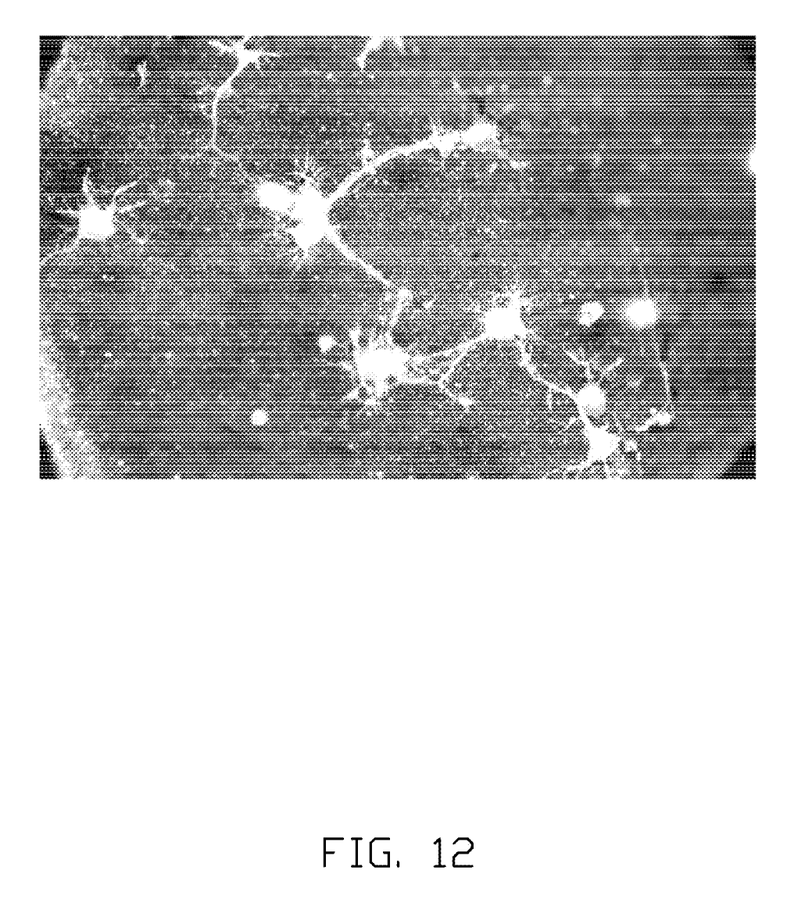
FIG. 12 shows an SEM image of the nerve graft, wherein the nerve network of the nerve graft are not dyed.

The neurites 24 can be dendrites or axons. Generally, the neurites 24 can grow in all directions from one nerve cell. Referring to FIG. 11 and FIG. 12, if there are a plurality of nerve cells 22 located one the surface of the cow blood serum layer, the neurites 24 from one nerve cell 22 would preferentially extend to adjacent nerve cells 22. Thus, growth directions of the neurites 24 can be guided by positions of the nerve cells 22. The nerve cells 22 can also be connected by the neurites 24 to form the nerve network. Cell growth factors can be provided by the cow blood serum layer for culturing the nerve cells 22. Alternatively, the carbon nanotube film structure cannot define the growth surrounding for the nerve cells 22, the nerve cells 22 can only be cultured on the surface of the carbon nanotube layer with cow blood serum layer thereon. The nerve network can only be located on the carbon nanotube layer with cow blood serum layer thereon and combined with the carbon nanotube layer.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

What is claimed is:

1. A method for making a nerve graft, the method comprising:

providing a lyophobic substrate, wherein the lyophobic substrate is a silica gel substrate or a substrate coated with silica gel;

making a carbon nanotube film structure comprising at least one drawn carbon nanotube film which is free-standing and comprises a plurality of carbon nanotube segments successively oriented along a fixed direction, and joined end-to-end by van der Waals attractive force therebetween along the fixed direction, wherein each carbon nanotube segment comprises a plurality of carbon nanotubes parallel to each other and combined by van der Waals attractive force therebetween, a majority of the carbon nanotubes are oriented along the fixed direction that is substantially parallel to a surface of the carbon nanotube film structure, and wherein the carbon nanotube film structure has a thickness of about 0.3 micrometers;

attaching the carbon nanotube film structure directly on a surface of the lyophobic substrate;

making a culture layer comprising the carbon nanotube film structure and a protein layer in direct contact with the carbon nanotube film structure, wherein the protein layer comprises a protein attached on the carbon nanotube film structure, a thickness of the protein layer is from about 0.3 micrometers to about 2 micrometers;

seeding a plurality of nerve cells on a surface of the protein layer away from the carbon nanotube film structure; and forming a nerve network by culturing the plurality of nerve cells until a plurality of neurites branch from the plurality of nerve cells and are connected between the plurality of nerve cells.

2. The method of claim 1, wherein the step of forming the nerve network further comprises connecting each of the plurality of nerve cells to one adjacent nerve cell of the plurality of nerve cells by at least one of the plurality of neurites.

3. The method of claim 1, wherein the plurality of neurites comprise dendrites and axons.

4. The method of claim 1, wherein the protein layer comprises soluble protein.

5. The method of claim 1, wherein the protein layer comprises blood serum of a mammal.

6. The method of claim 1, wherein the step of making the culture layer comprises:
soaking the carbon nanotube film structure with a protein solution comprising the protein to form the protein layer.

7. The method of claim 6, wherein the step of soaking the carbon nanotube film structure comprises a step of dipping the carbon nanotube film structure into the protein solution.

8. The method of claim 6, wherein the step of soaking the carbon nanotube film structure comprises a step of spraying the protein solution on the surface of the carbon nanotube film structure.

9. The method of claim 1, further comprising a step of introducing a poly-D-lysine layer on a surface of the protein layer away from the carbon nanotube film structure.

10. The method of claim 9, wherein the step of introducing the poly-D-lysine layer comprises a step of dipping the protein layer into a poly-D-lysine solution.

11. The method of claim 1, further comprising a step of sterilizing the protein layer.

12. The method of claim 11, wherein the protein layer is sterilized by means of an ultraviolet sterilization technology or a high temperature sterilization technology.

13. The method of claim 1, wherein the carbon nanotube film structure comprises a plurality of drawn carbon nanotube films, wherein adjacent carbon nanotube films are combined and attracted to each other only by van der Waals attractive force therebetween.

14. The method of claim 1, wherein the step of forming the nerve network further comprises culturing a majority of the plurality of neurites oriented along a preferred orientation.

15. The method of claim 1, wherein the plurality of carbon nanotubes in the carbon nanotube film structure are pure carbon nanotubes consisting primarily of carbon atoms.

16. The method of claim 1, wherein the plurality of nerve cells are seeded on the protein layer by spraying a solution comprising nerve cells to the surface of the protein layer, or by dipping the culture layer into said solution comprising nerve cells.

* * * * *